United States Patent [19]

Schmolka

[11] 4,206,198

[45] Jun. 3, 1980

[54] DENTIFRICE

[75] Inventor: Irving R. Schmolka, Grosse Ile, Mich.

[73] Assignee: BASF Wyandotte Corporation, Wyandotte, Mich.

[21] Appl. No.: 39,681

[22] Filed: May 16, 1979

[51] Int. Cl.² .......................... A61K 7/16; A61K 7/22
[52] U.S. Cl. ........................................ 424/49; 424/54
[58] Field of Search ..................................... 424/49–58

[56] References Cited

U.S. PATENT DOCUMENTS

| | | | |
|---|---|---|---|
| 2,677,700 | 5/1954 | Jackson et al. | 424/49 X |
| 2,773,801 | 12/1956 | Fox | 424/49 |
| 3,927,201 | 12/1975 | Baines et al. | 424/54 |
| 3,934,002 | 1/1976 | Haefele | 424/54 |
| 3,937,805 | 2/1976 | Harrison | 424/54 |
| 3,976,765 | 8/1976 | Nachtigal | 424/54 |
| 4,011,309 | 3/1977 | Lutz | 424/49 |
| 4,025,616 | 5/1977 | Haefele | 424/52 |
| 4,117,107 | 9/1978 | Shapiro et al. | 424/54 |
| 4,130,636 | 12/1978 | Tomlinson | 424/52 |

FOREIGN PATENT DOCUMENTS 2430280 1/1976 Fed. Rep. of Germany .
50-76243 6/1975 Japan .

OTHER PUBLICATIONS

Schmolka, J. Soc. Cosmet. Chem., (1974), 25(11): 593–607, Formulating High–Foaming Cosmetic Products.
Reng, Parfuem, Kosmet. (1976) 57(11): 307–316, Foaming Agents for Products for Oral and Dental Hygiene.

*Primary Examiner*—Shep K. Rose
*Attorney, Agent, or Firm*—John W. Linkhauer

[57] ABSTRACT

There is made a dentifrice containing a cationic antidecay agent plus, to provide adequate foaming properties without an unpleasant taste, a nonionic surfactant which is an ethoxylated adduct of $C_{15}$ or $C_{16}$ fatty alcohol in which EO units account for 50 to 75 percent of the molecular weight of the adduct.

4 Claims, No Drawings

DENTIFRICE

BACKGROUND OF THE INVENTION

1. Field of the Invention

This invention relates to a dentifrice composition, and in particular, to one which contains an effective amount of cationic anti-decay agent plus a nonionic surfactant which provides adequate foaming properties without imparting an unpleasant taste.

2. Description of the Prior Art

Including an anti-decay agent in a dentifrice (tooth powder or paste) is known. See, for example, U.S. Pat. No. 3,989,813, where there is provided a dentifrice containing 1,6-di-(p-chlorophenyl biguanidohexane) as an agent which inhibits the growth of many microorganisms such as *Lactobacillus acidophilus odontolyticus,* and U.S. Pat. No. 3,984,537, which teaches use of a non-toxic amino-cyano polymeric diguanide or salt thereof. The latter patent teaches that its polymeric diguanides are cationic but compatible with anionic substances and other materials usually present in oral preparations. The disclosures of the above-mentioned patents notwithstanding, it has not been usual to include in a dentifrice, especially in a toothpaste, an anti-decay agent of cationic nature, largely because it has been usual to employ as a part of the composition a high-foaming surfactant, and to be more specific, usually a high-foaming surfactant of anionic nature. In general, the use of an anionic surfactant for foam generation is not compatible with the use of a cationic agent for control of decay (caries); the two, if used together, will with rare exceptions react and cancel each other.

Including a dentifrice a nonionic surfactant with unobjectionable taste and considerable foaming properties is also not new. See, for example, the formulation designated "No. 9" on page 330 of *A Formulary of Cosmetic Preparations,* compiled by Michael and Irene Ash (Chemical Publishing Co., New York, 1977), in which 2 percent of "Pluronic F-87" surfactant is used in the making of a toothpaste. That particular formulation or recipe does not contain any cationic anti-decay agent. "Pluronic F-87" polyol is nonionic, a block copolymer with an internal block of PO units contributing an average molecular weight of 2,250 and external blocks of EO units which, between them, contribute approximately 70 percent of the molecular weight of the total molecule. It is known to chemists who are familiar with surfactants as perhaps the highest-foaming member of the family of "Pluronic" polyols. It is also not inexpensive to manufacture because its manufacture necessarily involves not one but two separate polymerization operations which are conducted at superatmospheric pressure and moderately elevated temperature. Another point of difference between "Pluronic F-87" and the nonionic surfactants used according to the present invention is that the latter are substantially more highly biodegradable than the former.

Reference may be had to the above-mentioned work by Michael and Irene Ash for examples of formulations known to be useful for making toothpaste. A typical toothpaste contains about 40 to 50 percent polishing agent, most usually dicalcium phosphate, possibly replaced in part by other mild abrasives such as chalk, clay, and other phosphates;

about 0.5 to 3 percent of detergent, most usually either 1.5 or 2 percent of sodium lauryl sulfate;

about 10 to 25 percent of sorbitol syrup (usually 70 percent active ingredient);

about 10 to 30 percent of glycerin, with the proviso that if either the sorbitol or the glycerin is omitted, the other one of the two is used liberally;

about 0.15 to 0.2 percent of sodium saccharin, although this is sometimes omitted or replaced with other sweetener;

about 0.5 to 3 percent of flavoring oils, usually about 1 percent or less, peppermint oil being popular;

about 1 to 2 percent of binding agent such as magnesium aluminum silicate (VEEGUM F), sodium carboxymethyl cellulose, methyl cellulose, Irish moss, etc., singly or in combination;

about 0.2 to 1 percent of a preservative such as methylparaben, propylparaben, or sodium benzoate;

and the remainder mostly water plus, in some cases, small amounts of other ingredients such as therapeutic agent, dye, etc.

In the field of nonionic surfactants made by oxyethylating fatty alcohols, fatty acids, fatty amides, fatty amines, or alkylphenols, the effects upon foaming properties of adding various numbers of oxyethylene units have been investigated—see page 336 of Surface Active Ethylene Oxide Adducts by Schoenfeldt (Pergamon Press, London, 1969). It reports the work of K. Tagawa et al. published in *Kogyo Kagaku Zasshi,* 65, 949–953 (1962), from which we know that various EO adducts of cetyl alcohol ($C_{16}H_{33}OH$) have been made and tested for foaming performance. The prior art does not, to my knowledge, contain any indication of the taste characteristics of these or other EO adducts of fatty alcohols.

SUMMARY OF THE INVENTION

There is made a dentifrice containing a cationic anti-decay agent plus, to provide adequate foaming properties without an unpleasant taste, a nonionic surfactant which is an ethoxylated adduct of $C_{15}$ or $C_{16}$ fatty alcohol in which EO units account for 50 to 75 percent of the molecular weight of the adduct.

DESCRIPTION OF THE PREFERRED EMBODIMENTS

There is made in accordance with the invention a dentifrice which contains as its detergent ingredient an ethoxylated adduct of $C_{15}$ or $C_{16}$ fatty alcohol in which EO units account for 50 to 75 percent, preferably about 62 percent, of the molecular weight of the adduct. This is based upon a discovery that, unlike the fatty alcohols containing 14 or fewer carbon atoms, the fatty alcohols which contain 15 or 16 carbon atoms yield oxyethylated adducts which have a mild, bland, or unobjectionable taste and are thus suitable for inclusion in a dentifrice composition. The adducts of $C_{15}$ or $C_{16}$ alcohols which are oxyethylated to a proper extent do, moreover, exhibit adequate or good foaming action, which the adducts made from alcohols containing 17 or more carbon atoms do not. It have discovered, thus, that there exists, in the case of the adducts made from $C_{15}$ or $C_{16}$ alcohols, an unpredicted and unpredictable combinatiion of satisfactory taste and adequate foam action. Therefore, such adducts made it possible to envisage the making and using of a dentifrice which contains both such adduct in an amount effective to provide the desired foaming action and an amount of a cationic anti-decay or anti-caries or bactericidal agent effective to suppress caries. The invention provides a way of using even certain ones of the cationic agents which could not hitherto be considered for use along with an anionic surfactant.

Thus, it may be stated that there is provided, according to the invention, a dentifrice which contains a foam-producing amount of a surfactant which is an adduct of a fatty alcohol containing 15 to 16 carbon atoms with a proportion of ethylene oxide such that 50 to 75 percent of the molecular weight of the adduct is attributable to oxyethylene units, plus an effective amount of an anti-decay agent which is of cationic nature, with the further proviso that a proportion of the ethylene oxide may be replaced with higher alkylene oxide such as propylene oxide and/or butylene oxide to the extent that such higher oxide accounts for up to 10 percent of the molecular weight of the adduct and is added either as an internal block or mixed with the ethylene oxide to form a heteric adduct. In other words, there is not used a block of higher-alkylene-oxide units which forms a cap, because it is necessary to obtain adequate foaming properties. In other words, according to the invention, there may be provided a dentifrice consisting essentially in weight percent of about:

40 to 50 percent of polishing agent;
0 to 21 percent of sorbitol;
0 to 30 percent of glycerol, with the proviso that the sum of the glycerol and sorbitol is 20 to 40 percent;
1 to 2 percent of binding agent;
0.2 to 1 percent of preservative;
0.5 to 3 percent of flavoring agent;
0 to 0.5 percent of sweetening agent;
an effective amount of an anti-decay agent of cationic nature;
0.5 to 3 weight percent of a foaming nonionic surfactant which is an adduct of the formula $$R-(OA)_n-H$$

where R is an alkyl radical containing 15 to 16 carbon atoms;
A is a bivalent alkylene radical containing 2 to 4 carbon atoms, such that individual OA units may be the same or different, and the number of OA units in which A contains 3 or 4 carbon atoms is such as to account for from 0 to 10 percent of the molecular weight of the adduct, and the positioning of OA units in which A contains 3 or 4 carbon atoms in the molecule is such that they are present either as a block proximate to the radical R or randomly distributed through the length of the chain indicated by portion $-(OA)_n-$ of the above formula;
n is a number such that said portion $-(OA)_n-$ accounts for 50 to 75 percent of the molecular weight of said adducts; and
the remainder substantially water.

Such a dentifrice has the novel combination of features that it has adequate foaming properties, contains a surfactant which is nonionic and is not only satisfactory in its taste properties but also substantially more highly biodegradable than the other nonionic surfactant sometimes hitherto used in toothpaste, and contains an effective amount of cationic anti-decay agent.

The cationic anti-decay agent may be a cationic surface-active germicide or antibacterial compound. Thus, agents such as diisobutylphenoxyethoxyethyl dimethyl benzyl ammonium chloride, benzyl dimethyl stearyl ammonium chloride, tertiary amines having one $C_{12}$ to $C_{18}$ fatty alkyl group and two polyoxyethylene groups attached to the nitrogen (the agent typically containing a total of 2 to 50 ethanoxy groups per molecule) and acid salts thereof may be used. Other known antibacterial agents which may be used include:

$N^1$-(4-chlorobenzyl)-$N^5$-(2,4-dichlorobenzyl) biguanide;
p-chlorophenyl biguanide;
4-chlorobenzhydryl biguanide;
4-chlorobenzhydrylguanylurea;
$N^3$-lauroxypropyl-$N^5$-p-chlorobenzylbiguanide;
1,6-di-(p-chlorophenylbiguanidohexane);
1-(lauryldimethylammonium)-8-(p-chlorobenzyldimethylammonium)-octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyramidine; and their non-toxic acid addition salts, particularly those where the anion includes a fluorine atom, such as: fluoride, monofluorophosphate, hexafluorosilicate and hexafluoroaluminate.

The dihydrogen fluoride is preferred. 1,6-di-(p-chlorophenylbiguanidohexane) dihydrogen fluoride is particularly preferred.

Such materials are used in an amount which will generally be in the range 0.01 percent to 5 percent by weight of the dentifrice.

Various other materials may be incorporated in the oral preparations of this invention. Examples are coloring or whitening agents, preservatives, solubilizing or compatibilizing agents, silicones, chlorophyll compounds and ammoniated material as urea, diammonium phosphate and mixtures thereof. These adjuvants, where present, are incorporated in the preparations in amounts which do not substantially adversely affect the properties and characteristics desired.

Any suitable flavoring or sweetening materials may also be employed. Examples of suitable flavoring constituents are flavoring oils, e.g., oils of spearmint, peppermint, wintergreen, sassafras, clove, sage, eucalyptus, marjoram, cinnamon, lemon and orange, and sodium methylsalicylate. Suitable sweetening agents include sucrose, lactose, maltose, sorbitol, sodium cyclamate, perillartine and saccharin. Suitably, the flavor and sweetening agents may together comprise from 0.01 percent to 5 percent or more of the preparation.

The invention is illustrated by the following specific examples, in which parts are by weight.

EXAMPLE 1

A dentifrice is made which contains:

| Ingredient | Part |
|---|---|
| Glycerin | 30.0 |
| Carboxymethyl cellulose | 1.7 |
| Sweetener | 0.2 |
| Sodium benzoate | 0.5 |
| Water | 17.0 |
| Nonionic Adduct (Surfactant B, defined hereinbelow) | 1.5 |
| Calcium carbonate | 47.8 |
| Oil of cloves | 0.8 |
| 4-Chlorobenzhydryl biguanide | 0.5 |

The resultant dentifrice has good foaming action, satisfactory taste, and an effective content of a cationic anti-caries agent.

EXAMPLE 2

A dentifrice is made which contains:

| Ingredient | Part |
| --- | --- |
| Ethanol | 3.0 |
| Nonionic Adduct (Surfactant B, defined hereinbelow) | 2.0 |
| Water | 24.0 |
| Sorbitol | 11.5 |
| Glycerin | 12.0 |
| Polishing agent $Ca_3(PO_4)_2.2H_2O$ | 43.5 |
| Silica | 1.5 |
| CMC (food grade) | 0.5 |
| Sweetener | 0.5 |
| Preservative | 0.5 |
| Peppermint oil | 0.3 |
| Anise oil | 0.2 |
| 1,6-di(p-chlorophenyl)biguanidohexane | 0.5 |

The resultant dentifrice has good foaming action, satisfactory taste, and an effective content of a cationic anti-caries agent.

The assertion, that the adducts discussed above will make it possible for the dentifrices to have the desirable combination of properties indicated above, is based upon experiments which will be explained below.

Taste tests were conducted on various ethoxylated adducts of fatty alcohols containing different numbers of carbon atoms. The adducts were ones that had been ethoxylated to the extent necessary to yield a surfactant of near-maximal foaming power (EO units accounting for about 60 weight percent of the molecular weight of the adduct). The tasters agreed that the products that were based upon fatty alcohols containing 14 or fewer carbon atoms exhibited tastes that were bitter or undesirable, whereas the ones based upon $C_{15}$ or $C_{16}$ fatty alcohol were mild or bland or tasteless.

In the work mentioned immediately above, commercially available fatty alcohols were used, and these invariably contain a small percentage, usually not over 7 percent and sometimes not over 1 percent, of impurities, which are usually in large part other fatty alcohols with a different but similar number of carbon atoms. Thus, in the case of the fatty alcohols containing even numbers of carbon atoms, there are the "Alfol" alcohols, sold by Continental Oil Company, Saddle Brook, N.J., which are indicated in literature published by that company as having purities ranging from 98.7 to 99.3 percent. A commercially manufactured material, designated as being a $C_{15}$ fatty alcohol is made by Shell Chemical Company, Houston, Texas, as "Neodol 5" alcohol; and analysis of such material revealed a purity in excess of 95 percent and a content of $C_{14}$ alcohols on the order of 3.3 percent.

The taste tests reveal that the bitterness-producing potential of the fatty alcohols with 12 to 14 carbon atoms is not so high that it is necessary to take special measures, ones beyond those ordinarily employed in making a $C_{15}$ or $C_{16}$ fatty alcohol of the degree of purity which characterize the products now marketed, to exclude them from the fatty-alcohol material which is alkoxylated in order to produce the adducts which are made for use in compounding the dentifrice of the present invention. In making the dentifrice of the present invention, it is satisfactory to make the detergent component from a fatty-alcohol material containing at least 95 percent by weight of fatty alcohol containing 15 to 16 carbon atoms.

Tests have also been conducted to establish that the bland-tasting detergents mentioned above also exhibit foam-forming properties which are sufficient to make them suitable for inclusion in a dentifrice as the detergent component thereof. In a first series of tests, using aqueous solutions containing 0.1 percent of surfactant in a revolving cylinder test at 25 revolutions per minute and a temperature of 105 degrees Fahrenheit (40.6 degrees Centigrade), two known high-foaming nonionic surfactants of the $$HO(C_2H_4O)_x(C_3H_6O)_y(C_2H_4O)_xH$$

type were compared with two detergent materials which were adducts of $C_{15}$ alcohol and ethylene oxide. In the Table below, Surfactant A is an adduct of $C_{15}$ alcohol plus sufficient ethylene oxide that oxyethylene units account for 58 percent of the molecular weight of the resulting adduct, and Surfactant B is an otherwise identical adduct in which the oxyethylene units account for 62 percent of the molecular weight of the adduct. Commercial Nonionic Surfactant X is "Pluronic F-87" polyol, which was defined above in the discussion of the prior art, and Nonionic Surfactant Y is another member of the same family of polyols, one with a typical molecular weight of the polyoxypropylene hydrophobe of 2,250 and external blocks of oxyethylene units which, between them, contribute approximately 60 percent of the molecular weight of the total molecule.

Table I

| Surfactant | Foam Generated Milliliters |
| --- | --- |
| Commercial Nonionic Surfactant X | 550 |
| Commercial Nonionic Surfactant Y | 550 |
| Surfactant A | 500 |
| Surfactant B | 600 |

Further foaming tests were conducted with Surfactants A and B or others similar to them but with greater oxyethylene content (C, 66 percent; D, 68 percent; E, 70 percent) and with the use of higher concentrations of surfactant, and the results are presented below in Table II.

Table II

| Surfactant | Concentration, % | Foam Generated, Milliliters |
| --- | --- | --- |
| A | 0.5 | 550 |
| B | 0.5 | 700 |
| C | 0.5 | 800 |
| A | 1.0 | 450 |
| B | 1.0 | 800 |
| C | 1.0 | 820 |
| C | 10.0 | 650 |
| D | 10.0 | 680 |
| E | 10.0 | 670 |

The embodiments of the invention in which an exclusive property or privilege is claimed are as follows:

1. A dentifrice which contains a foam-producing amount of a surfactant which is an adduct of fatty alcohol containing 15 to 16 carbon atoms with a proportion of ethylene oxide such that 50 to 75 percent of the molecular weight of the adduct is attributable to oxyethylene units, plus an effective amount of an anti-decay agent which is of cationic nature, with the further proviso that a proportion of the ethylene oxide may be replaced with higher alkylene oxide such as propylene oxide and/or butylene oxide to the extent that such higher oxide accounts for up to 10 percent of the molecular weight of the adduct and is added either as an internal block or mixed with the ethylene oxide to form a heteric adduct.

2. A dentifrice as defined in claim 1, wherein said surfactant is an adduct of $C_{15}$ fatty alcohol with ethylene oxide such that the ethylene oxide units of said adduct account for about 62 percent of its molecular weight.

3. A dentifrice consisting essentially in weight percent of about:
   40 to 50 percent of polishing agent;
   0 to 21 percent of sorbitol;
   0 to 30 percent of glycerol, with the proviso that the sum of the glycerol and sorbitol is 20 to 40 percent;
   1 to 2 percent of binding agent;
   0.2 to 1 percent of preservative;
   0.5 to 3 percent of flavoring agent;
   0 to 0.5 percent of sweetening agent;
   an effective amount of an anti-decay agent of cationic nature;
   0.5 to 3 weight percent of a detergent which is an adduct of the formula $$R-(OA)_n-H$$

where R is an alkyl radical containing 15 to 16 carbon atoms;

A is a bivalent alkylene radical containing 2 to 4 carbon atoms, such that individual OA units may be the same or different, and the number of OA units in which A contains 3 or 4 carbon atoms is such as to account for from 0 to 10 percent of the molecular weight of the adduct, and the positioning of OA units in which A contains 3 or 4 carbon atoms in the molecule is such that they are present either as a block proximate to the radical R or randomly distributed through the length of the chain indicated by portion $-(OA)_n-$ of the above formula;

n is a number such that said portion $-(OA)_n-$ accounts for 50 to 75 percent of the molecular weight of said adducts; and the remainder substantially water.

4. A dentifrice as defined in claim 3 wherein said detergent is an adduct of $C_{15}$ fatty alcohol with ethylene oxide such that the ethylene oxide units of said adduct account for about 62 percent of its molecular weight.

* * * * *